US00PP08954P

United States Patent [19]

Gruppe et al.

[11] Patent Number: Plant 8,954

[45] Date of Patent: Oct. 25, 1994

[54] CHERRY ROOTSTOCK GI 148/1

[75] Inventors: Werner Gruppe, Linden/Hessen; Hanna Schmidt, Ahrensburg, both of Fed. Rep. of Germany

[73] Assignee: Inter-Plant Patent Marketing, Inc., Niagara-On-The-Lake, Canada

[21] Appl. No.: 922,123

[22] Filed: Jul. 29, 1992

[51] Int. Cl.[5] ..... A01H 5/00

[52] U.S. Cl. ..... Plt./37

[58] Field of Search ..... Plt. 37

[56] References Cited

PUBLICATIONS

R. L. Perry (1987) In: Rootstucks for fruit crops, R. C. Rom & R. F. Carlson, eds., pp. 251–254.

Registration documents for 173/9 and 148/2.

German publication "GIESSEN 1991" Red Book.

German publication "GIESSEN 1991" Green Book.

Newspaper clipping dated Sturday, Feb. 15, 1992.

Cherry Rootstock NC–140, 1990.

Miscellaneous German Test Data.

*Primary Examiner*—James R. Feyrer

*Assistant Examiner*—Bruce Campell

*Attorney, Agent, or Firm*—Dykema Gossett

[57] ABSTRACT

The new and distinct cultivar of cherry rootsock, which has been given the designation GI 148/1 produces a tree which is generally erect and medium strong in growth, and which upon grafting produces a dwarf tree.

3 Drawing Sheets

FIELD OF THE INVENTION

The present invention relates generally to cherry trees and more specifically to a new and distinct variety of cherry hybrid tree which is particularly useful as a rootstock.

BACKGROUND OF THE INVENTION

The new and distinct variety of cherry hybrid tree of the present invention was bred by the inventor as a cross of *Prunus cerasus* cv. Schattenmorelle with *Prunus canescens* in Giessen, Germany. It has been successfully assexually propagated by softwood cuttings with mist at Giessen University, Giessen, Germany, and has been observed to remain true to the description set forth herein. In one test planting in Kassel, Germany, 148/1 was chip-budded with a mean success of 72%.

SUMMARY OF THE INVENTION

The new and distinct cultivar of cherry rootstock, which has been given the designation GI 148/1 produces a tree which is generally erect and medium strong in growth, and which upon grafting produces a dwarf tree.

DETAILED DESCRIPTION OF THE INVENTION

Figure 1:
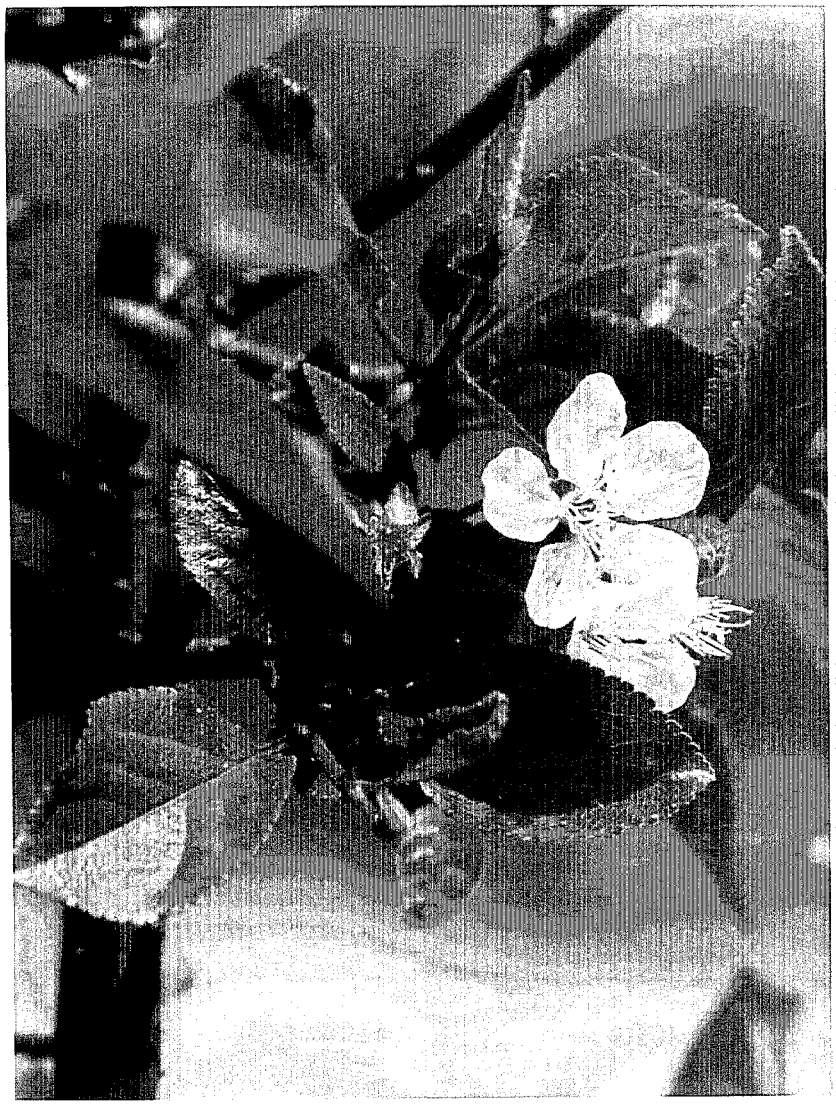
FIG. 1 illustrates a branch and bloom of GI 148/1.
Figure 2:
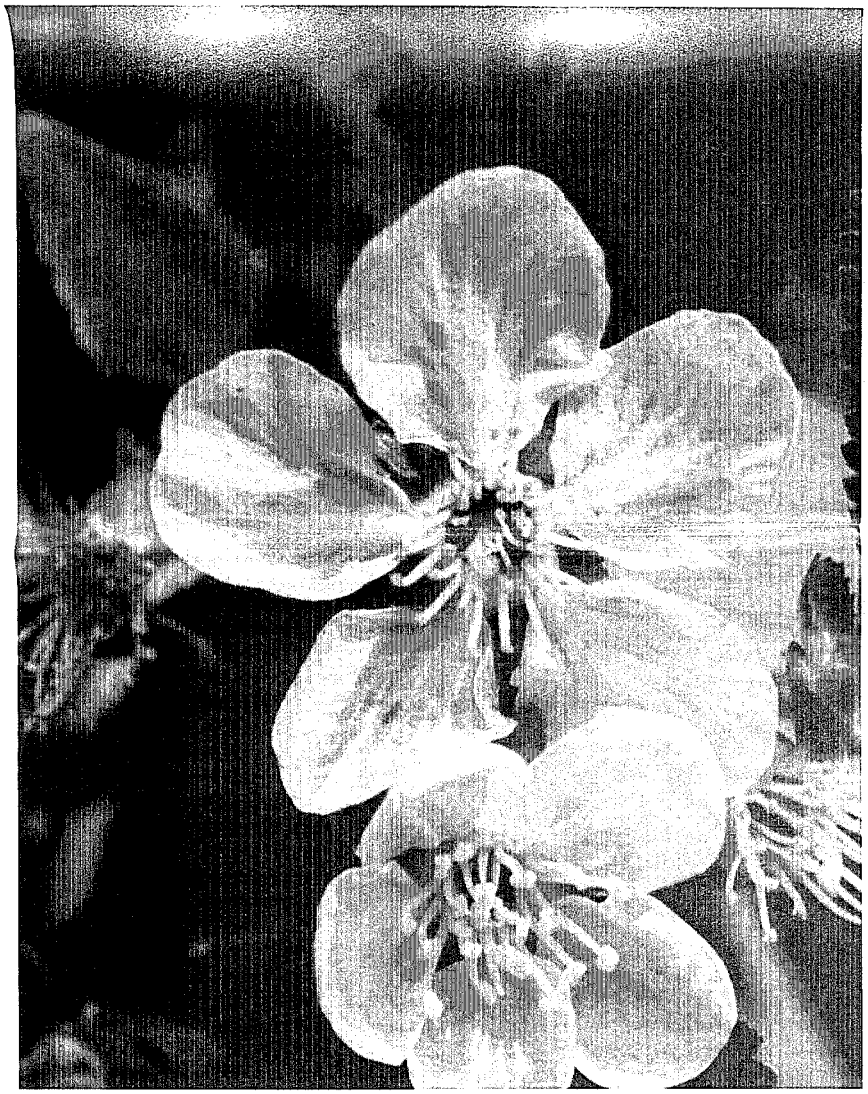
FIG. 2 illustrates GI 148/1 flowers.
Figure 3:
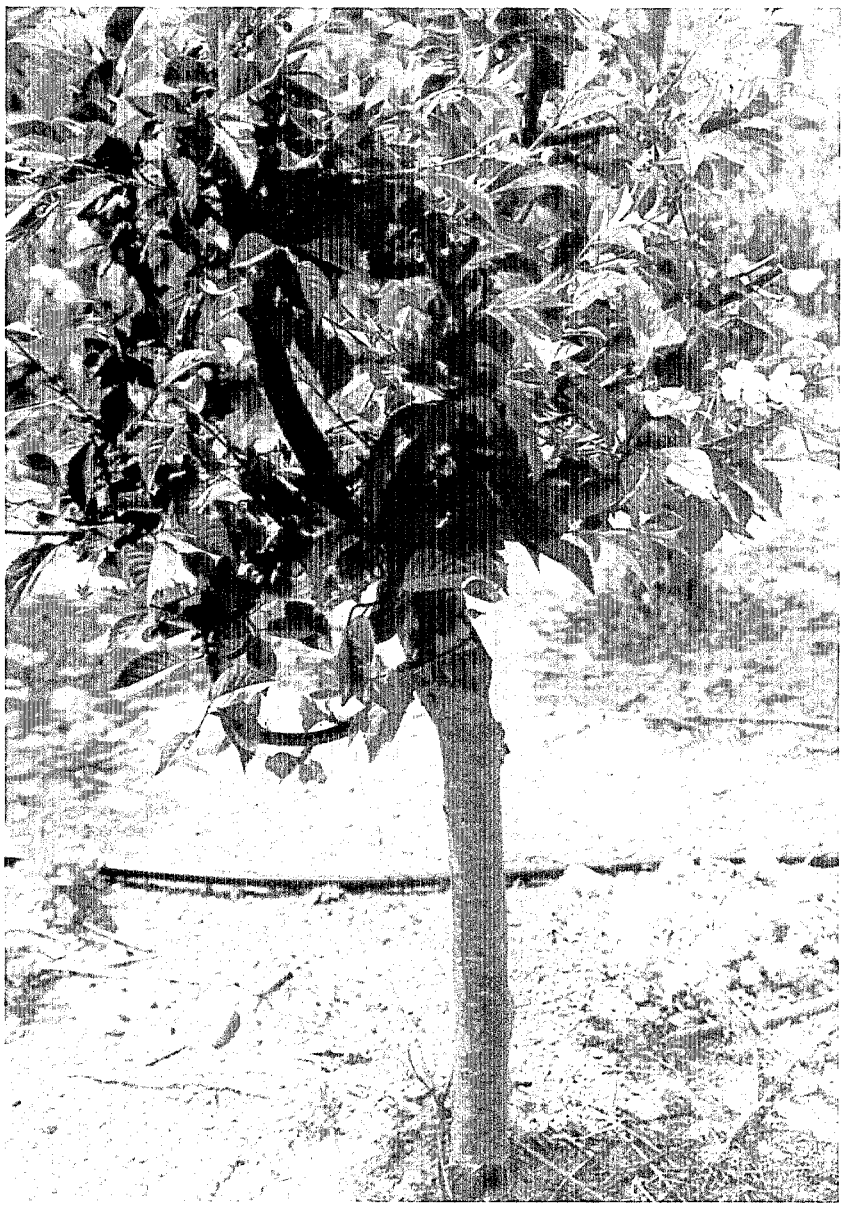
FIG. 3 is a whole tree view of 148/1.

GI 148/1 as used as a rootstock for sweet cherry trees induces dwarfing to a significant degree. In comparison with rootstock F12/1, GI 148/1 produces 67 percent of growth, as measured as the weight of the upper tree parts of cv. Hedelfinger after 12 years in orchards near Giessen, Germany. Precosity, high production of fruit and yield efficiency, good 100-fruit weight and no or very few suckers were induced. GI 148/1 as a rootstock confers earlier and heavier bearing to the scion as compared to F12/1. In one trial it induced a yield in the variety "Hedelfinger" in the 5th leaf of 5.0 kg/tree (cf.

F12/1: 0.2 kg/tree) and in the 7th leaf of 22.1 kg/tree (Cf. F12/1: 5.7 kg/tree). As a mean of 7 years, 100-fruit weight of "Hedelfinger" grafted on 148/1 was 748 grams, and on F12/1 it was only 735 grams.

GI 148/1 itself is generally erect and medium strong in growth. After ten growing seasons near Giessen, Germany, GI 148/1 demonstrated a height of 3.60 meters and a width of 3.20 meters. The growth reduction induced by 148/1 is more pronounced in good soil; in poor soil trees reach nearly the same height as F12/1. Comparison of tree height, 6th leaf, variety "Buttners Rote Knorpel" at Witzenhausen-Wendershausen (poor soil) and Hattersheim (very good soil) is as follows:

| | Rootstock | | |
|---|---|---|---|
| Location | 148/1 | F12/1 | Colt |
| Witzenhausen | 350 cm | 354 cm | 340 cm |
| Hattersheim | 388 cm | 482 cm | 465 cm |

The following varieties of sweet and sour cherries have been successfully grafted onto GI 148/1: Hedelfinger Riesenkirsche, Büttners Rote Knorpel, Grosse Schwarze Knorpel, Van, Gold, Ulster, Bing, Early Burlat, Emperor Francis, Querfurter Königskirsche, Napoleon, Rainier, Sam, Schmidt, merton Glory, Alma, Meckenheimer Frühe, Oktavia, Valeska, Spalding, Schneiders Späte Knorpel, Stella, Vega, Vic, Viva, Windsor, Hudson, Lambert; Montmorency, Meteor, Rubinweichsel, Morellenfeuer, North Star, Schattenmorelle, Rheinische Schattenmorelle, Ludwigs FrUM/u/ he, Leitzkauer, Nabella, Successa, Schwäbische Weinweichsel. No graft incompatibility is presently known.

148/1 is tolerant to both viruses PNRV and PDV and medium sensitive to "Pfeffinger disease." It is tolerant to water logging and has sufficient frost hardiness.

Ploidy of 148/1 is believed to be 2n=3x=24. The ploidy status of the parents has been investigated by isoemzyme analysis and is tetraploid (2n=4x=32) for the mother plant=*Prunus certasus* "Schattenmorelle", and diploid (2n=2x=16) for the father plant=*Prunus canescens.*

Leaves:

*Overall shape.*—Ovate.

*Length-to-*width ratio.—1.6.

*Apex shape.*—Acute to slightly acuminate.

*Base shape.*—Rounded, slightly acute.

*Leaf serration.*—Doubly serrate leaf margin, secondary notches are small.

*Venation.*—Pinnate, 11–13 veins, mainly alternate.

*Stipules.*—Prominent, at base of petiole during growing season.

*Glands.*—Rounded, attached to base of blade or adjacent petiole, 2–3 prominent plus 1–2 rudimentary.

*Pubescence.*—Very slightly pubescent on adaxial surface (top), slightly pubescent on abaxial surface, most along veins.

*Color.*—Green, Fan 3 143A (R.H.S. — The Royal Horticultural Society Colour Chart).

Branches:

*Thickness of one year branch.*—2.0 mm diameters.

*Color.*—Redbrown-grey.

*Canopy area.*—88% of F12/1.

*Lenticels.*—On 1-year old branches are light cream colored, 0.5 mm diameter. Color of 1-year old branch: greyed organe, Fan 4, 166-A (R.H.S.). Color of 2-year old branch: greyed orange, Fan 4, 165-A (R.H.S.). Color of 3-year old branch: greyed orange, Fan 4, 165-A (R.H.S.). Color of 4-year old branch: greyed orange, Fan 4, 175-A (R.H.S.).

Buds: No ornamental value.

*Shape.*—Conical, somewhat rounded, adpressed, 2–3 mm long.

*Bud scales.*—Overlapping bud scales, smooth, with prominent leaf scars.

Flowers: Late flowering.

*Abundance.*—Heavy.

*Petal color.*—White.

*Petal shape.*—Nearly round.

*Petal length.*—1:1.

*Filaments.*—Coarse, erect.

Fruits:

*Size.*—Medium.

*Form.*—Round.

*Stem length.*—Medium.

*Skin color.*—Red.

*Flesh Color.*—Yellow.

*Juice color.*—Light.

*Flesh texture.*—Very soft.

*Taste.*—Bitter sweet.

*Stone size.*—Medium.

Overall vigor:

*Ungrafted.*—Medium strong vigor.

*Suckers.*—No suckers in unworked condition; few suckers grafted with "Hedelfinger".

*Support.*—No support required.

Root system: Exceptional total length of roots and a high percentge of very thin roots.

Survey of growth data: Growth of clones, not grafted, 60 kilometers south of Giessen, Germany.

*Planted.*—Autumn 1972; cut down to the ground Spring 1982.

*Measurements.*—After 10 years: — height 3.6 meters. — width 3.2 meters. — depth 3.5 meters. — fresh weight 32.8 kg.

*General.*—Medium strong growing, broad. Growth of clones grafted with "Hedelfinger Riesenkirsche" 60 kilometers south of Giessen, Germany.

*Planted.*—Nov. 1975.

*Rooted out.*—Apr. 1988 (after 12 years in orchard) mean values of two trees compared with means values of three trees F12/1 standard.

| | GI 148/1 | F12/1 |
|---|---|---|
| Height of Crown (Winter 87/88) | 3.3 m | 5.2 m |
| Width of Crown (Winter 87/88) | 5.2 m | 6.2 m |
| Stem Cross Sectional Area of Variety (Winter 87/88) | 492 $cm^2$ | 503 $cm^2$ |
| Stem Cross Sectional Area of Rootstock (Winter 87/88) | 266 $cm^2$ | 486 $cm^2$ |
| Fresh Weight of Plant Parts Above Ground (April 88) | 118 kg | 176 kg |
| Weight in Percent | 67% | 100% |

Characteristics of leaves: (situated on the wood of that year) measured 1977=in the 5th leaf and compared with F12/1:

*Mean length of leaves was.*—5.5 cm (F12/1: 10.7 cm).

*Mean width of leaves was* .—3.4 cm (F12/1: 5.3 cm).

*Mean length of petioles was.*—0.9 cm (F12/1: 2.6 cm).

*Dates.*—Of blooming were systematically studied for three years as follows: Heldenbergen, 60 km south of Giessen: 1973: Apr. 26. 1974: Apr. 9. 1975: Apr. 29.

Branch dimensions (For a single GI 148/1 plant in the ungrafted condition measured in the end of 1977=after the 5th leaf; in brackets data for F12/1 for comparison.):

*Mean length of* 1-*year-old branches.*—22.8 cm (19.8).

*Mean length of* 2-*year-old branches.*—17.2 cm (35.0).

*Mean length of* 3-*year-old branches.*—50.8 cm (63.2).

*Mean diameter of* 1-*year-old branches.*—2.0 mm (3.4).

*Mean diameter of* 2-*year-old branches.*—3.2 mm (5.8).

*Mean diameter of* 3-*year-old branches.*—5.8 mm (10.1).

*Mean no. of branches from* 2-*year-old branches.*—0.2 (0.7).

*Mean no. of branches from* 3-*year-old branches-*.—(2.4).

*Mean no. of nodes of* 2-*year-old branches.*—8.4 (15.3).

*Mean no. of nodes of* 3-*year-old branches.*—21.4 (22.4).

*Mean angle of* 3-*year old branches.*—61.0 (59.7).

*Mean angle of* 4-*year old branches.*—55.0 (58.3).

Enzyme polymorphism: (Studied by horizontal starch gel electrophoresis of leaf tissue of 8 loci.) The results for the siblings of 148 are:

| Locus | 148/1 | 148/8 |
|---|---|---|
| Aconitase-2 | 24 | 2 |
| Alkoholdehydrogenase-1 | 112 | 1 |
| Isocitratdehydrogenase-2 | 112 | 112 |
| Leucinaminopeptidase-1 | 34 | 34 |

-continued

| Locus | 148/1 | 148/8 |
|---|---|---|
| 5-Phosphogluconat-Dehydrogenase-1 | 112 | 112 |
| 6-Phosphogluconat-Dehydrogenase-2 | 122 | 122 |

-continued

| Locus | 148/1 | 148/8 |
|---|---|---|
| Phophoglucose-Isomerase-2 | 224 | 224 |
| Phosphoglucomutase-2 | 25 | 25 |

Whate is claimed is:

1. A new and distinct variety of charry hybrid tree as described herein.

* * * * *